(12) United States Patent  
Zhang et al.

(10) Patent No.: US 8,014,863 B2  
(45) Date of Patent: Sep. 6, 2011

(54) HEART ATTACK OR ISCHEMIA DETECTOR

(75) Inventors: Yi Zhang, Blaine, MN (US); Richard Fogoros, Pittsburg, PA (US); Julie Thompson, Circle Pines, MN (US); Bruce H. KenKnight, Maple Grove, MN (US); Michael J. Pederson, Minneapolis, MN (US); Abhilash Patangay, Little Canada, MN (US); Tamara Colette Baynham, Blaine, MN (US); Yatheendhar D. Manicka, Woodbury, MN (US); Scott T. Mazar, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1207 days.

(21) Appl. No.: 11/625,045

(22) Filed: Jan. 19, 2007

(65) Prior Publication Data

US 2008/0177194 A1    Jul. 24, 2008

(51) Int. Cl.  
*A61B 5/02* (2006.01)

(52) U.S. Cl. .......................... 607/18; 600/513

(58) Field of Classification Search ............ 607/18  
See application file for complete search history.

(56) References Cited

U.S. PATENT DOCUMENTS

| | | | |
|---|---|---|---|
| 3,703,900 A | 11/1972 | Holznagel | |
| 3,716,059 A | 2/1973 | Welborn et al. | |
| 3,799,147 A | 3/1974 | Adolph et al. | |
| 3,910,260 A | 10/1975 | Sarnoff et al. | |
| 4,004,577 A | 1/1977 | Sarnoff | |
| 4,432,374 A | 2/1984 | Osanai | |
| 4,562,846 A | 1/1986 | Cox et al. | |
| 4,679,144 A | 7/1987 | Cox et al. | |
| 4,773,401 A | 9/1988 | Citak et al. | |
| 4,798,211 A | 1/1989 | Goor et al. | |
| 4,821,735 A | 4/1989 | Goor et al. | |
| 4,830,006 A * | 5/1989 | Haluska et al. | 607/4 |
| 4,924,875 A | 5/1990 | Chamoun | |
| 5,020,540 A | 6/1991 | Chamoun | |
| 5,050,612 A | 9/1991 | Matsumura | |

(Continued)

FOREIGN PATENT DOCUMENTS

EP    0867146 A1    9/1998

(Continued)

OTHER PUBLICATIONS

"International Application Serial No. PCT/US2008/000720, International Search Report mailed Oct. 27, 2008", 5 pgs.

(Continued)

*Primary Examiner* — Carl H Layno  
*Assistant Examiner* — Jessica Sarcione  
(74) *Attorney, Agent, or Firm* — Schwegman, Lundberg & Woessner, P.A.

(57) ABSTRACT

A system including an implantable trigger event detector and an implantable ischemia detector. The implantable trigger event detector is adapted to detect at least one first condition and to output a responsive trigger signal including information about whether the first condition has been detected. The implantable ischemia detector is adapted to detect a second condition indicative of one or more physiologic cardiovascular events in a subject that are indicative of ischemia. The ischemia detector is coupled to the trigger event detector to receive the trigger signal, and the ischemia detector is enabled upon the trigger signal indicating that the first condition has been detected.

28 Claims, 6 Drawing Sheets

U.S. PATENT DOCUMENTS

| | | | |
|---|---|---|---|
| 5,054,496 A | 10/1991 | Wen et al. | |
| 5,083,563 A * | 1/1992 | Collins | 607/4 |
| 5,199,428 A | 4/1993 | Obel et al. | |
| 5,228,449 A | 7/1993 | Christ et al. | |
| 5,313,953 A | 5/1994 | Yomtov et al. | |
| 5,330,505 A | 7/1994 | Cohen | |
| 5,342,406 A | 8/1994 | Thompson | |
| 5,370,666 A * | 12/1994 | Lindberg et al. | 607/16 |
| 5,466,245 A | 11/1995 | Spinelli et al. | |
| 5,485,849 A | 1/1996 | Panescu et al. | |
| 5,505,202 A | 4/1996 | Mogi et al. | |
| 5,520,191 A | 5/1996 | Karlsson et al. | |
| 5,743,267 A | 4/1998 | Nikolic et al. | |
| 5,758,652 A | 6/1998 | Nikolic | |
| 5,792,066 A | 8/1998 | Kwong | |
| 5,819,741 A | 10/1998 | Karlsson et al. | |
| 5,824,021 A | 10/1998 | Rise | |
| 5,833,621 A | 11/1998 | Panescu et al. | |
| 5,891,045 A | 4/1999 | Albrecht et al. | |
| 6,016,443 A | 1/2000 | Ekwall et al. | |
| 6,021,350 A | 2/2000 | Mathson | |
| 6,038,469 A | 3/2000 | Karlsson et al. | |
| 6,047,206 A | 4/2000 | Albrecht | |
| 6,076,015 A | 6/2000 | Hartley et al. | |
| 6,102,874 A | 8/2000 | Stone et al. | |
| 6,108,577 A | 8/2000 | Benser | |
| 6,171,256 B1 | 1/2001 | Joo et al. | |
| 6,217,525 B1 | 4/2001 | Medema et al. | |
| 6,223,082 B1 | 4/2001 | Bakels et al. | |
| 6,233,486 B1 | 5/2001 | Ekwall et al. | |
| 6,246,910 B1 | 6/2001 | Bonnet et al. | |
| 6,256,538 B1 | 7/2001 | Ekwall | |
| 6,264,606 B1 | 7/2001 | Ekwall et al. | |
| 6,277,078 B1 | 8/2001 | Porat et al. | |
| 6,314,323 B1 | 11/2001 | Ekwall | |
| 6,319,205 B1 | 11/2001 | Goor et al. | |
| 6,360,123 B1 | 3/2002 | Kimchi et al. | |
| 6,381,493 B1 | 4/2002 | Stadler et al. | |
| 6,409,675 B1 | 6/2002 | Turcott | |
| 6,454,719 B1 | 9/2002 | Greenhut et al. | |
| 6,456,880 B1 | 9/2002 | Park et al. | |
| 6,468,263 B1 | 10/2002 | Fischell et al. | |
| 6,473,646 B2 | 10/2002 | Sun et al. | |
| 6,480,733 B1 | 11/2002 | Turcott | |
| 6,491,639 B1 | 12/2002 | Turcott | |
| 6,493,579 B1 | 12/2002 | Gilkerson et al. | |
| 6,512,949 B1 | 1/2003 | Combs et al. | |
| 6,514,195 B1 | 2/2003 | Ferek | |
| 6,561,984 B1 | 5/2003 | Turcott | |
| 6,572,557 B2 | 6/2003 | Tchou et al. | |
| 6,575,912 B1 | 6/2003 | Turcott | |
| 6,589,188 B1 | 7/2003 | Street et al. | |
| 6,600,949 B1 | 7/2003 | Turcott | |
| 6,604,000 B2 | 8/2003 | Lu | |
| 6,609,023 B1 | 8/2003 | Fischell et al. | |
| 6,643,548 B1 | 11/2003 | Mai et al. | |
| 6,666,826 B2 | 12/2003 | Salo et al. | |
| 6,721,591 B2 | 4/2004 | Wei et al. | |
| 6,827,690 B2 | 12/2004 | Bardy | |
| 6,889,081 B2 | 5/2005 | Hsu | |
| 6,937,899 B2 | 8/2005 | Sheldon et al. | |
| 7,039,462 B2 | 5/2006 | Pastore et al. | |
| 7,171,258 B2 | 1/2007 | Goode | |
| 7,181,268 B2 | 2/2007 | Sheldon et al. | |
| 7,181,269 B1 | 2/2007 | Kroll | |
| 7,190,996 B2 | 3/2007 | Jarverud | |
| 7,215,992 B2 | 5/2007 | Stahmann et al. | |
| 7,215,997 B2 | 5/2007 | Yu et al. | |
| 7,364,547 B2 | 4/2008 | Stahmann et al. | |
| 7,415,307 B2 | 8/2008 | Sharma et al. | |
| 7,479,112 B2 | 1/2009 | Sweeney et al. | |
| 7,512,439 B1 | 3/2009 | Farazi | |
| 7,539,533 B2 | 5/2009 | Tran | |
| 7,577,478 B1 | 8/2009 | Kroll et al. | |
| 2001/0037069 A1 | 11/2001 | Carlson et al. | |
| 2002/0002389 A1 | 1/2002 | Bradley et al. | |
| 2002/0111551 A1 | 8/2002 | Van Erlach et al. | |
| 2002/0123772 A1 | 9/2002 | Sun et al. | |
| 2002/0143262 A1* | 10/2002 | Bardy | 600/508 |
| 2002/0161412 A1 | 10/2002 | Sun et al. | |
| 2003/0004549 A1 | 1/2003 | Hill et al. | |
| 2003/0009197 A1 | 1/2003 | Helland et al. | |
| 2003/0055461 A1 | 3/2003 | Girouard et al. | |
| 2003/0100925 A1 | 5/2003 | Pape et al. | |
| 2003/0125774 A1 | 7/2003 | Salo | |
| 2003/0158492 A1* | 8/2003 | Sheldon et al. | 600/508 |
| 2003/0199956 A1 | 10/2003 | Struble et al. | |
| 2003/0208240 A1 | 11/2003 | Pastore et al. | |
| 2003/0216657 A1 | 11/2003 | Holmstrom et al. | |
| 2004/0122478 A1* | 6/2004 | Stadler et al. | 607/17 |
| 2004/0127792 A1 | 7/2004 | Siejko et al. | |
| 2004/0215092 A1 | 10/2004 | Fischell et al. | |
| 2005/0004476 A1 | 1/2005 | Payvar et al. | |
| 2005/0043675 A1 | 2/2005 | Pastore et al. | |
| 2005/0159666 A1 | 7/2005 | Pearce et al. | |
| 2005/0197674 A1 | 9/2005 | McCabe et al. | |
| 2005/0256417 A1 | 11/2005 | Fischell et al. | |
| 2005/0283195 A1 | 12/2005 | Pastore et al. | |
| 2005/0288721 A1 | 12/2005 | Girouard et al. | |
| 2006/0009811 A1 | 1/2006 | Sheldon et al. | |
| 2006/0052717 A1 | 3/2006 | Mugler et al. | |
| 2006/0116593 A1 | 6/2006 | Zhang et al. | |
| 2006/0184060 A1 | 8/2006 | Belalcazar et al. | |
| 2006/0241357 A1 | 10/2006 | Chirife | |
| 2006/0253044 A1 | 11/2006 | Zhang et al. | |
| 2006/0259087 A1 | 11/2006 | Baynham et al. | |
| 2006/0282000 A1 | 12/2006 | Zhang et al. | |
| 2006/0287684 A1 | 12/2006 | Baynham et al. | |
| 2007/0038256 A1 | 2/2007 | Maschke | |
| 2007/0043393 A1 | 2/2007 | Brockway et al. | |
| 2007/0049835 A1 | 3/2007 | Goode | |
| 2007/0054871 A1 | 3/2007 | Pastore et al. | |
| 2007/0093720 A1 | 4/2007 | Fischell et al. | |
| 2007/0129639 A1 | 6/2007 | Zhang et al. | |
| 2007/0150005 A1 | 6/2007 | Sih et al. | |
| 2007/0150015 A1 | 6/2007 | Zhang et al. | |
| 2007/0162081 A1 | 7/2007 | Yu et al. | |
| 2007/0179392 A1 | 8/2007 | Zhang | |
| 2007/0203524 A1 | 8/2007 | Sheldon et al. | |
| 2007/0208263 A1 | 9/2007 | John et al. | |
| 2007/0276453 A1 | 11/2007 | Hill et al. | |
| 2007/0299356 A1 | 12/2007 | Wariar et al. | |
| 2008/0058661 A1 | 3/2008 | Bardy | |
| 2008/0081354 A1 | 4/2008 | Qu et al. | |
| 2008/0082135 A1 | 4/2008 | Arcot et al. | |
| 2008/0091138 A1 | 4/2008 | Pastore et al. | |
| 2008/0139954 A1 | 6/2008 | Day et al. | |
| 2008/0177156 A1 | 7/2008 | Zhang et al. | |
| 2008/0177191 A1 | 7/2008 | Patangay et al. | |
| 2008/0188762 A1 | 8/2008 | John et al. | |
| 2008/0188763 A1 | 8/2008 | John et al. | |
| 2008/0228094 A1 | 9/2008 | Audet et al. | |
| 2008/0287818 A1 | 11/2008 | Shelchuk et al. | |
| 2009/0025459 A1 | 1/2009 | Zhang et al. | |
| 2009/0043223 A1 | 2/2009 | Zhang et al. | |
| 2009/0048528 A1 | 2/2009 | Hopenfeld et al. | |
| 2009/0082682 A1 | 3/2009 | Fischell et al. | |
| 2009/0082781 A1 | 3/2009 | Tran et al. | |
| 2009/0124916 A1 | 5/2009 | Sweeney et al. | |
| 2009/0171228 A1 | 7/2009 | Fischell et al. | |
| 2009/0177103 A1 | 7/2009 | Bharmi | |

FOREIGN PATENT DOCUMENTS

| | | |
|---|---|---|
| EP | 1118307 A1 | 7/2001 |
| EP | 1348463 A1 | 10/2003 |
| WO | WO-02/40096 A1 | 5/2002 |
| WO | WO-03/020367 A1 | 3/2003 |
| WO | WO-03/089033 A1 | 10/2003 |
| WO | WO-2006/081336 A2 | 8/2006 |
| WO | WO-2006081336 A2 | 8/2006 |
| WO | WO-2008/088897 A2 | 7/2008 |

OTHER PUBLICATIONS

"International Application Serial No. PCT/US2008/000720, Written Opinion mailed Oct. 27, 2008", 9 pgs.

Amende, I., "Hämodynamik unter Ischämia: Diastolische Phase. [Hemodynamics in Ischemia: Diastolic Phase]", *Zeitschrift für Kardiologie*, 73(Suppl 2), (w/ English Abstract), (1984), 127-133.

Dzwonczyk, R., et al., "Myocardial electrical impedance responds to ischemia and reperfusion in humans", *IEEE Transactions on Biomedical Engineering*, 51(12), (2004), 2206-2209.

Kochiadakis, G. F., "Autonomic Nervous System Activity Before and During Episodes of Myocardial Ischemia in Patients with Stable Coronary Artery Disease During Daily Life", *Pacing and Clinical Electrophysiology*, 23(12), (2000), 2030-2039.

Krayenbühl, H. P., "Hämodynamik unter Ischämie. Systolische Phase. [Hemodynamics in ischemia. Systolic phase]", *Zeitschrift für Kardiologie*, 73(Suppl 2), (w/ English Abstract), (1984), 199-125.

McCloskey, D. I., et al., "Chapter 5: Cardiorespiratory Integration", *Vagal Control of the Heart : Experimental Basis and Clinical Implications*, vol. 7, Levy, M. N., et al., Editors, Futura Publishing Company, Inc., (1994), 65-76.

Migeotte, P. F., et al., "A Novel Algorithm for the Heart Rate Variability Analysis of Short-Term Recordings: Polar Representation of Respiratory Sinus Arrhythmia", *Computers and Biomedical Research*, 32(1), (1999), 56-66.

Migeotte, P. F., et al., "Microgravity alters respiratory sinus arrhythmia and short-term heart rate variability in humans", *Am J Physiol Heart Circ Physiol.*, 284(6), (2003), H1995-2006.

Pomeranz, B., et al., "Assessment of autonomic function in humans by heart rate spectral analysis", *Am J Physiol.*, 248(1 Pt 2), (1985), H151-H153.

Salerno, D. M., "Seismocardiography for Monitoring Changes in Left Ventricular Function During Ischemia.", *Chest*, 100(4), (1991), 991-993.

Saul, J. P., et al., "Transfer function analysis of autonomic regulation. II. Respiratory sinus arrhythmia", *Am J Physiol.*, 256(1 Pt 2), (1989), H153-H161.

Sroka, K., et al., "Heart Rate Variability in Myocardial Ischemia During Daily Life", *Journal of Electrocardiology*, 30(1), (1997), 45-56.

Sroka, K., "On the genesis of myocardial ischemia.", *Z Kardiol.*, 93(10), (2004), 768-783.

Triedman, J. K., et al., "Respiratory sinus arrythmia: time domain characterization using autoregressive moving average analysis", *Am J Physiol.* Jun. 1995;268(6 Pt 2):, (1995), H2232-H2238.

"European Application No. 08724646.8, Office Action mailed on Dec. 9, 2009", 4 pgs.

Takahashi, et al., "Inhibitory effects of hyperglycemia on neural activity of the vagus in rats", Intensive Care Medicine (2003), 29:309-311, (2003).

\* cited by examiner

HEART ATTACK OR ISCHEMIA DETECTOR

This application is related to commonly assigned, U.S. patent application Ser. No. 11/625,003, entitled "Ischemia Detection Using Heart Sound Timing," filed Jan. 19, 2007, now issued as U.S. Pat. No. 7,736,319, and to commonly assigned, copending, U.S. patent application Ser. No. 11/624,974, entitled "Ischemia Detection Using Pressure Sensor," filed Jan. 19, 2007, both of which are incorporated herein by reference.

TECHNICAL FIELD

The field generally relates to implantable medical devices and, in particular, but not by way of limitation, to systems and methods for detecting myocardial ischemia.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. In addition to electrical events, CFM devices may measure hemodynamic parameters related to chamber filling and contractions. Ischemia occurs when blood flow to cardiac muscles decreases below the metabolic requirements of the heart. Detecting ischemia early is critical to the health of the patient and allows early initiation of treatment. Cardiac muscle cells that are ischemic are electrically irritable and may be more susceptible to abnormal heart rhythms (e.g., fibrillation). Further, ischemia impairs the pumping function of the heart. If left untreated the underlying cause of ischemia which is commonly artherosclerotic disease may lead to myocardial infarction (i.e., heart attack).

SUMMARY

This document discusses, among other things, systems and methods for monitoring cardiac function of a patient or subject. In Example 1, a system includes an implantable trigger event detector and an implantable ischemia detector. The implantable trigger event detector is adapted to detect at least one first condition and to output a responsive trigger signal including information about whether the first condition has been detected. The implantable ischemia detector is adapted to detect a second condition indicative of one or more physiologic cardiovascular events in a subject that are indicative of ischemia. The ischemia detector is coupled to the trigger event detector to receive the trigger signal, and the ischemia detector is enabled upon the trigger signal indicating that the first condition has been detected.

In Example 2, the system of Example 1 optionally includes an implantable cardiac signal sensing circuit in communication with the trigger event detector, and the ischemia detector is enabled upon the trigger signal indicating that a heart rate exceeds a predetermined heart rate threshold value.

In Example 3, the system of Examples 1-2 optionally include an implantable cardiac signal sensing circuit in communication with the trigger event detector, and the ischemia detector is optionally enabled upon the trigger signal indicating that a rate of change in heart rate exceeds a predetermined heart rate threshold value.

In Example 4, the system of Examples 1-3 optionally include an implantable cardiac signal sensing circuit in communication with the trigger event detector, and the ischemia detector is optionally enabled upon the trigger signal indicating a decrease in heart rate variability (HRV).

In Example 5, the system of Examples 1-4 optionally include an implantable cardiac signal sensing circuit and an implantable respiration sensor in communication with the trigger event detector, and the ischemia detector is optionally enabled upon the trigger signal indicating a decrease in respiratory sinus arrhythmia (RSA).

In Example 6, the system of Examples 1-5 optionally includes an implantable patient activity sensor and a timer circuit coupled to the trigger event detector, and the ischemia detector is optionally enabled upon the trigger signal indicating a decrease in patient activity level within a predetermined period of time.

In Example 7, the system of Examples 1-6 optionally includes an implantable patient activity sensor and an implantable respiration sensor in communication with the trigger event detector, and the ischemia detector is optionally enabled upon the trigger signal indicating at least one of an increase in patient exertion and an increase in patient stress.

In Example 8, the system of Examples 1-7 optionally includes an implantable cardiac signal sensing circuit in communication with the trigger event detector, and the ischemia detector is optionally enabled upon the trigger signal indicating an abnormal cardiac rhythm.

In Example 9, the system of Example 1-8 optionally includes a timer circuit coupled to the trigger event detector, and the ischemia detector is optionally enabled by the trigger event detector using a circadian rhythm.

In Example 10, the trigger event detector and the ischemia detector of Examples 1-9 are optionally included in an implantable medical device (IMD), the system further includes an external device adapted to communicate with the IMD, and the ischemia detector is enabled by the trigger event detector in response to a communication with the external device.

In Example 11, the ischemia detector of Examples 1-10 optionally includes one or more implantable sensors from the group consisting of: a heart sound sensor, a cardiac blood pressure sensor, a cardiac signal sensing circuit adapted to sense intracardiac electrograms, a subcutaneous ECG sensing circuit, a cardiac wall motion sensor, a transthoracic impedance sensor, an intracardiac impedance sensor, a chemical sensor, an oxygen sensor, an accelerometer, and a temperature sensor.

In Example 12, the ischemia detector of Examples 1-11 optionally includes at least one first implantable sensor, configured to produce a first electrical sensor signal related to one or more physiologic cardiovascular events in a subject that are indicative of ischemia, and an implantable posture sensor configured to produce an electrical signal related to posture of the subject. The ischemia detector is configured to trend the first electrical sensor signal in relation to posture of the subject.

In Example 13, the ischemia detector of Examples 1-12 optionally includes at least one first implantable sensor, configured to produce a first electrical sensor signal related to one or more physiologic cardiovascular events in a subject that are indicative of ischemia, and an implantable activity sensor configured to produce an electrical signal related to activity of the subject. The ischemia detector is configured to trend the first electrical sensor signal in relation to activity of the subject.

In Example 14, the ischemia detector of Examples 1-13 optionally includes at least one first implantable sensor, configured to produce a first electrical sensor signal related to one or more physiologic cardiovascular events in a subject that are indicative of ischemia, and an implantable cardiac signal sensing circuit to produce an electrical signal related to heart rate of a patient. The ischemia detector is adapted to trend the first electrical sensor signal in relation to heart rate of the subject.

In Example 15, the trigger event detector and the ischemia detector of Examples 1-14 are optionally included in an implantable medical device (IMD) that includes an audible alarm circuit coupled to the ischemia detector, and the ischemia detector is configured to provide an audible alarm if an episode of myocardial ischemia is declared upon detecting the second condition.

In Example 16, the trigger event detector and the ischemia detector of Examples 1-15 are optionally included in an implantable medical device (IMD), and the system of the Examples optionally includes an external device adapted to communicate with the IMD. The IMD is configured to communicate an indication of myocardial ischemia to the external device.

In Example 17, the system of Examples 1-16 optionally includes an external device that includes a remote server in communication with the IMD over a communications or computer network.

In Example 18, the system of Examples 1-17 optionally includes a memory, in communication with the ischemia detector, to store a log containing information related to ischemia for a patient.

In Example 19, the trigger event detector and the ischemia detector of Examples 1-18 are optionally included in an IMD that further includes a therapy circuit coupled to the ischemia detector. The ischemia detector is configured to initiate a device therapy if an episode of myocardial ischemia is declared upon detecting the second condition.

In Example 20, a method includes sensing one or more sensor signals produced by implantable sensors where the sensor signals include physiologic cardiovascular information, determining at least one first condition, and, upon detecting the first condition, enabling detection of a second condition related to one or more physiologic cardiovascular events in a subject that are indicative of myocardial ischemia.

In Example 21, the method of Example 20 optionally includes sampling the sensor signals at a first sampling rate to establish a baseline for the sensor signals and wherein enabling detection of the second condition includes enabling sampling of the sensor signals at a different second sampling rate.

In Example 22, determining the first condition in Examples 20-21 optionally includes detecting at least one physiologic event from the group consisting of: an increase in heart rate that exceeds a predetermined heart rate threshold, an increase in a rate of change in heart rate exceeds a predetermined heart rate threshold value, a decrease in heart rate variability (HRV), a decrease in respiratory sinus arrhythmia (RSA), an abnormal cardiac rhythm, a predetermined decrease in patient activity level within a predetermined period of time, an increase in at least one of patient exertion and patient stress, and a time that is predetermined according to a patient circadian rhythm.

In Example 23, determining the first condition in Examples 20-22 optionally includes determining a circadian rhythm of the subject.

In Example 24, determining the first condition in Examples 20-23 optionally includes determining that an enable for detecting the second condition is communicated from an external device.

In Example 25, detecting the second condition in Examples 20-24 optionally includes detecting one or more of: an ST segment deviation, a change in a cardiac activation sequence, a change in one or more heart sound features, a change in blood pressure from an established baseline blood pressure, a change in right ventricle and left ventricle synchrony, a change in morphology of a sensed cardiac depolarization signal, a decrease in cardiac blood oxygen saturation, a change in cardiac wall motion, a change in transthoracic impedance, a change in intracardiac impedance, and a change in cardiac temperature without an accompanying detected increase in patient exertion level.

In Example 26, the method of Examples 20-25 optionally include sampling the sensor signals, trending the sensor signals in the presence of physiologic noise, and using the trending to remove physiologic noise from the sampled signals.

In Example 27, the method of Examples 20-26 optionally include communicating an alarm if an episode of myocardial ischemia is declared upon detecting the second condition.

In Example 28, the method of Examples 20-27 optionally include updating an ischemia log for a patient if an episode of myocardial ischemia is declared upon detecting the second condition.

In Example 29, the method of Examples 20-28 optionally include initiating a device therapy if an episode of myocardial ischemia is declared upon detecting the second condition.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

An implantable medical device (IMD) may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

The IMDs may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Monitoring of electrical signals related to cardiac activity may provide early, if not immediate, diagnosis of ischemia.

Figure 1:
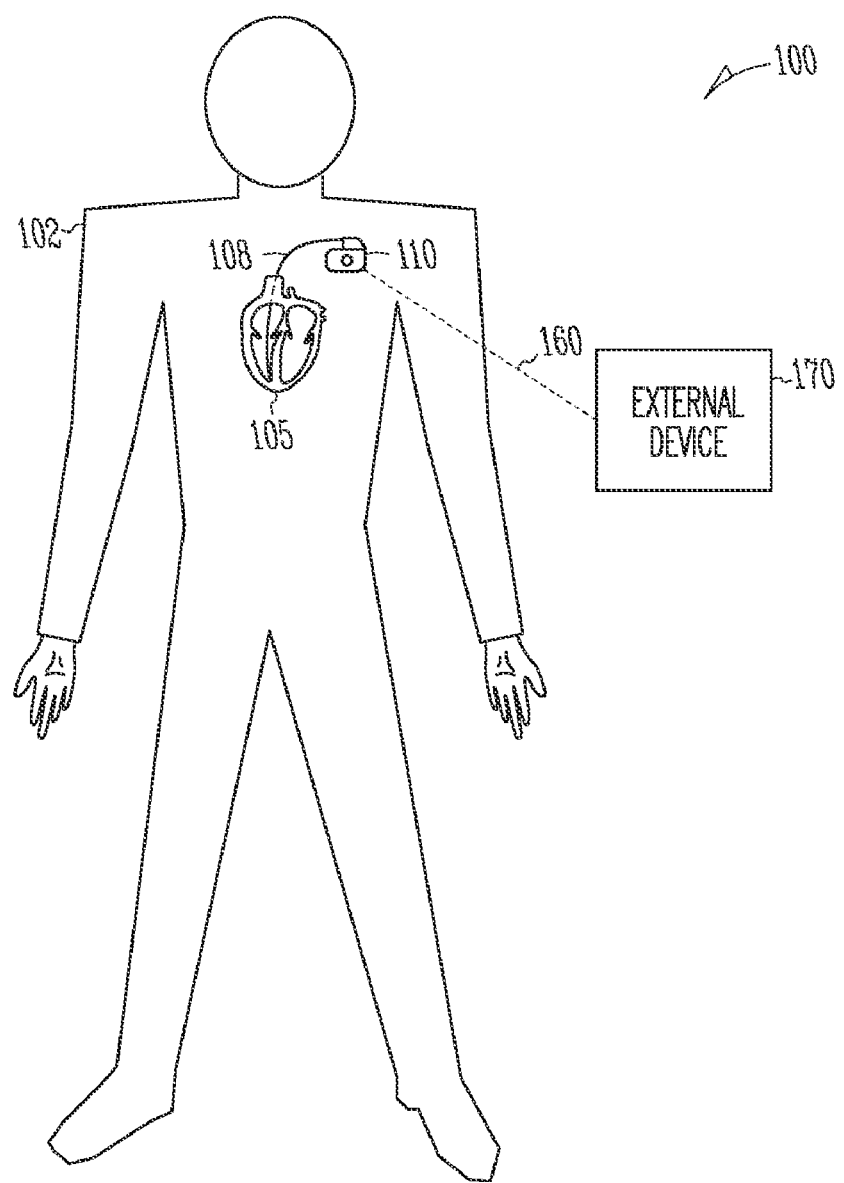
FIG. 1 is a block diagram of portions of a system that uses an implantable medical device (IMD).

FIG. 1 is a block diagram of portions of a system 100 that uses an implantable medical device (IMD) 110. As one example, the system 100 shown is used to treat a cardiac arrhythmia. The IMD 110 typically includes an electronics unit coupled by a cardiac lead 108, or additional leads, to a heart 105 of a patient 102 or subject, or otherwise associated with the heart 105. Examples of IMD 110 include, without limitation, a, pacemaker, a cardioverter, a defibrillator, a cardiac resynchronization therapy (CRT) device, and other cardiac monitoring and therapy delivery devices, including cardiac devices that include or work in coordination with neurostimulating devices, drugs, drug delivery systems, or other therapies. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing intrinsic or other electrical activity of the heart 105.

Figure 2:
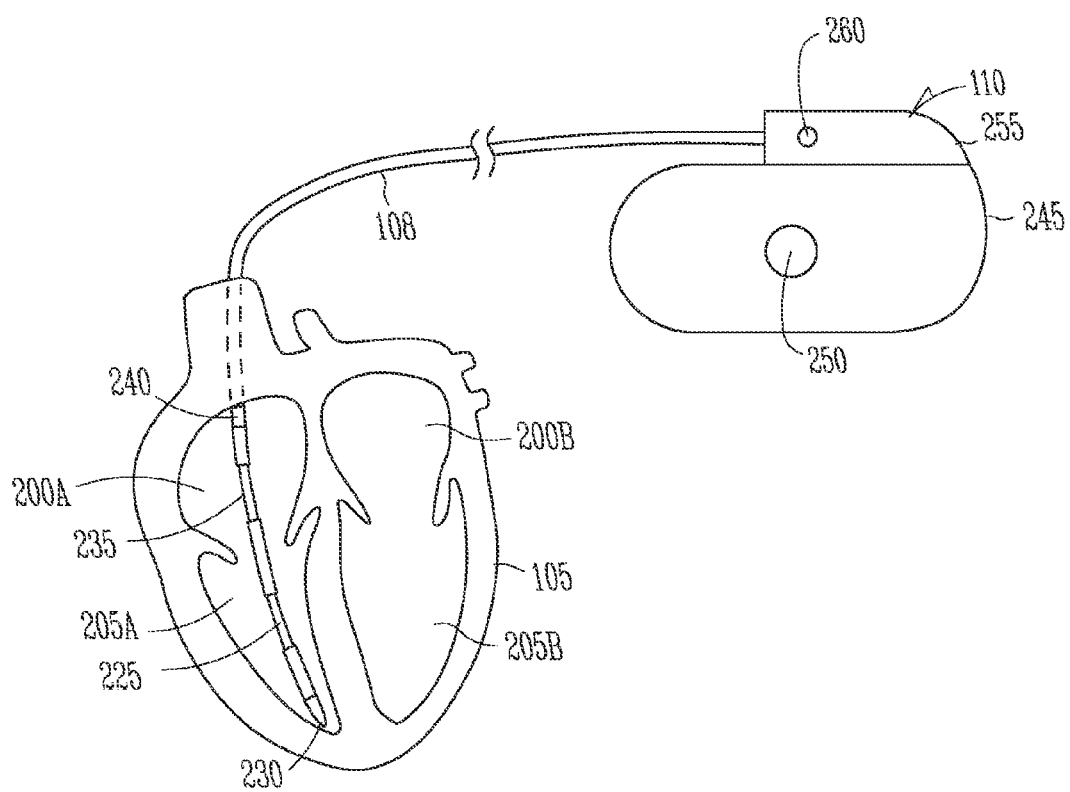
FIG. 2 illustrates an IMD coupled by one or more leads to a heart.

FIG. 2 illustrates an IMD 110 coupled by one or more leads 108 to heart 105. Heart 105 includes a right atrium 200A, a left atrium 200B, a right ventricle 205A, and a left ventricle 205B. Lead 108 includes electrodes (electrical contacts, such as ring electrode 225 and tip electrode 230) disposed in a right ventricle 205A of heart 105 for sensing signals, or delivering pacing therapy, or both, to the right ventricle 205A. Lead 108 also includes one or more electrodes for placement in the right atrium 200A, such as ring electrode 235 and ring electrode 240, for sensing electrical cardiac signals, delivering pacing therapy, or both sensing signals and delivering pacing therapy. Sensing and pacing allows the IMD 110 to adjust timing of the chamber contractions. For example, IMD 110 can adjust the timing of ventricular contractions with respect to the timing of atrial contractions delay by sensing a contraction in the right atrium 200A and pacing the right ventricle 205A at the desired atrial-ventricular (AV) delay time. The IMD also includes can electrode 250 formed on the IMD can 245, and header electrode 260 formed on the IMD header 255.

The IMD 110 optionally also includes additional leads and electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Optionally, lead 108 includes two leads containing two or more electrodes each. In an example, a first lead includes a tip electrode located in the apex of the right ventricle 205A and a first ring electrode located proximal to the tip electrode. A second lead includes a tip electrode located in the right atrium 200A and a ring electrode located in the right atrium 200A proximal to the tip electrode.

Optionally, IMD 110 includes an additional cardiac lead that includes ring electrodes for placement in a coronary vein extending along a wall of the left ventricle 205B. A lead placed in the left ventricle 205B and a lead placed in the right ventricle 205A may be used to optionally provide resynchronization therapy to the heart 105.

Figure 3A:
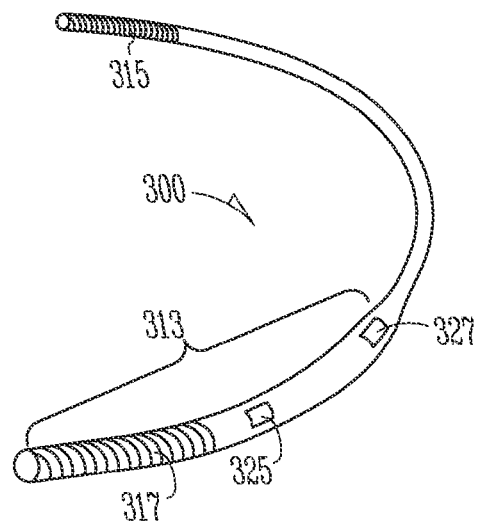
FIGS. 3A-B show an example of an IMD that does not use intravascular leads to sense cardiac signals.
Figure 3B:
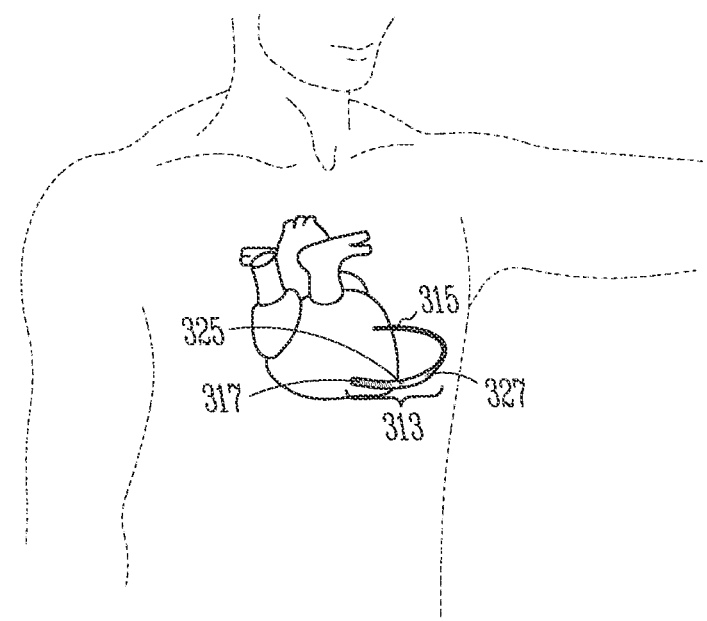

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrodes. FIGS. 3A-B show an example of an IMD 300 that does not use intravascular leads to sense cardiac signals. FIG. 3A shows that the IMD 300 includes a thicker end 313 to hold the power source and circuits. The IMD 300 also includes electrodes 325 and 327 for remote sensing of cardiac signals. Cardioversion/defibrillation is provided through electrodes 315 and 317. FIG. 3B shows an example of the IMD 300 positioned within a patient.

The majority of heart attacks (acute myocardial infarction) are caused by a rupture of vulnerable plaque, such as plaque developed due to atherosclerosis, causing a sudden coronary occlusion which typically leads to an acute medical emergency. A reduction in mortality due to heart attack can be achieved with reperfusion therapy, but success depends on the duration of the coronary occlusion before reperfusion therapy. The critical time for treatment is the first couple of hours after the onset of the symptoms of the heart attack, and early detection of myocardial ischemia is advantageous to the health of the patient.

Evidence of myocardial ischemia in a patient can become manifest in various ways. Occurrences of coronary blood flow occlusion typically result in an immediate increase in heart rate and a decrease in myocardial shortening, particularly in an ischemic heart-wall segment. Dyssynchrony in ventricular contractions also often occurs. Sometimes, abnormalities are detectable in an electrocardiograph (ECG) within thirty seconds to one minute after the occlusion. Myocardial ischemia depresses the peak negative rate of change of pressure (dP/dt) in the left-ventricle (LV) and also depresses the LV peak positive dP/dt. Myocardial ischemia may eventually lead to elevation of the S-T segment of the QRST cardiac activation sequence. A plurality of sensors can be used to detect a series of events related to ischemia. The probability that a patient has indeed experienced an ischemic event increases with the number of events in the series that are detected.

Implantable cardiac rhythm management (CRM) devices are sometimes equipped with implantable sensors that have the capability to detect various physiological variables associated with cardiac and pulmonary function. These sensors are typically used in applications such as rate responsive pacing and advanced patient management functions, such as remote patient monitoring and remote triggering of device therapy for example. Because myocardial ischemia can result in changes in the various physiological variables, these sensors may also be used for early detection of myocardial ischemia. Thus, the specificity of ischemia detection can be improved by detecting a series of ischemia-related events using a plurality of sensors where each sensor measures a part of the series of events. A difficulty in using such sensors is that it is costly from a battery energy standpoint to run the sensors and implement the algorithms used in the detection.

Figure 4:
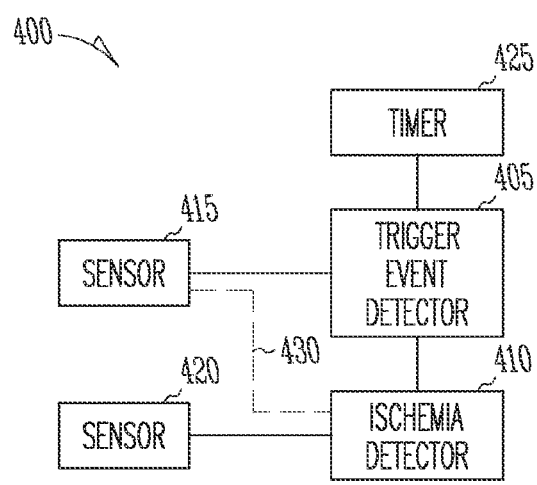
FIG. 4 is a block diagram of portions of an example of a system to detect myocardial ischemia.

FIG. 4 shows a block diagram of portions of an example of a system 400 to detect myocardial ischemia. The system 400 includes an implantable trigger event detector 405 and an implantable ischemia detector 410. The trigger event detector 405 detects a first condition and outputs a responsive trigger signal. The trigger signal includes information about whether a first condition has been detected. The ischemia detector 410 is coupled to the trigger event detector 405 and receives the trigger signal. The ischemia detector 410 is enabled upon the trigger signal indicating that the first condition has been detected.

In some examples, the first condition includes a physiologic condition of the patient that may indicate that the patient has experienced myocardial ischemia. The first condition may be a highly sensitive indication of ischemia (i.e., the first condition detection is most likely over-inclusive of physiologic events that indicate ischemia), but need not be specific to ischemia. Once enabled, the ischemia detector 410 detects a second condition indicative of one or more physiologic cardiovascular events in a patient, or subject, that indicate ischemia. The second condition is preferably more specific to myocardial ischemia than the first condition. Enabling the ischemia detector 410 can include powering-on at least a portion of the ischemia detector 410. Enabling can also include causing a branch to execute instructions in an ischemia detection module.

Modules can be software, hardware, firmware or any combination thereof. Multiple functions can be performed in one or more modules as desired, and the embodiments described are merely examples. The software and/or firmware are typically executed on a digital signal processor, application specific integrated circuit (ASIC), microprocessor, or other type of processor. The processor may operate as part of an implantable medical device (IMD).

The first condition may include one or more physiologic events. The events may include a detected physiologic change that may indicate a change in patient neural activity. An implantable sensor 415 may be arranged in electrical communication with the trigger event detector 405 to detect the event or events. In some examples, the trigger event detector 405 establishes a baseline for a sensor output signal and the first condition is detected when a change from the established baseline occurs. The baseline may be established recurrently, such as periodically for example.

In some examples, the implantable sensor 415 includes an implantable cardiac signal sensing circuit in communication with the trigger event detector, and the first condition includes a heart rate of a subject exceeding a predetermined heart rate threshold value. In some examples, the first condition includes a rate of change in a heart rate of a subject exceeds a predetermined heart rate threshold value.

Electrodes placed within the right ventricle of the heart provide a signal of impedance versus time. This intracardiac impedance waveform can be signal processed to obtain a measure of the time interval beginning with a paced or spontaneous QRS complex (systole marker) and ending with a point where the impedance signal crosses the zero axis in the positive direction following the QRS complex. The resulting time interval is inversely proportional to the contractility of the heart. Systems and methods to measure intracardiac impedance are described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference.

Heart rate variability (HRV) refers to the variability of the time intervals between successive heart beats during a sinus rhythm. In some examples of the system 400, the first condition includes a detected decrease in HRV. A patient with a low amount of measured HRV implies that the patient may have a decreased ability to compensate for changes in arterial pressure. Systems and methods to measure HRV are described in Spinelli et al., U.S. Pat. No. 5,466,245, entitled "Method and Apparatus to Continuously Optimize the A-V Delay in a Dual Chamber Pacemaker," filed Nov. 15, 1994, which is incorporated herein by reference.

In some examples, the first condition includes detection of an abnormal cardiac rhythm. An abnormal cardiac rhythm can be detected using an assessment of heart rhythm stability when a subject experiences a sudden increase in heart rate. Examples of methods and systems to detect abnormal heart rhythms and assess the stability of the rhythms are found in Gilkerson et al., U.S. Pat. No. 6,493,579, entitled "System and Method for Detection Enhancement Programming," filed Aug. 20, 1999, which is incorporated herein by reference.

In some examples, an abnormal cardiac rhythm is detected by comparing the morphology of a sensed cardiac signal to a morphology template stored in a memory. In some examples, the morphology of a sensed cardiac depolarization is compared to a template of a known normal or abnormal depolarization morphology (such as normal sinus rhythm, ventricular tachyarrhythmia, or supra-ventricular tachyarrhythmia) stored in memory. For example, a template can be created for a patient using a CRM by providing electrical energy pulses to the supra-ventricular region of the patient's heart. The resulting cardiac complexes are then sensed and used to create a template for use in a morphology-based cardiac signal classification algorithm. Systems and methods of creating templates for a morphology-based algorithm are described in Hsu, U.S. Pat. No. 6,889,081, entitled "Classification of Supra-ventricular and Ventricular Cardiac Rhythms Using Cross Channel Timing Algorithm," filed Jul. 23, 2002, which is incorporated herein by reference.

A plurality of implantable sensors 415 may be arranged in electrical communication with the trigger event detector 405 to detect the first condition event or events. In some examples, the system 400 includes an implantable cardiac signal sensing circuit and an implantable respiration sensor in communication with the trigger event detector, and the first condition includes a decrease in respiratory sinus arrhythmia (RSA). RSA refers to the change in heart rate of a subject between patient inhalation and exhalation. RSA is the natural cycle of arrhythmia that occurs through the influence of breathing on the flow of sympathetic and vagus impulses to the sinoatrial node. The rhythm of the heart is primarily under the control of the vagus nerve, which regulates heart rate and the force of contraction. The vagus nerve activity is dampened and heart rate begins to increase when a breath is inhaled. When exhaled, vagus nerve activity increases and the heart rate begins to decrease. A reduction of the difference in heart rate between inhalation and exhalation may be an indication of a reduction in a patient's vagal response.

An example of an implantable respiration sensor is a transthoracic impedance sensor to measure minute respiration volume. An approach to measuring transthoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference.

In some examples, the system 400 includes an implantable patient activity sensor and an implantable respiration sensor in electrical communication with the trigger event detector 405. The first condition includes an increase in patient exertion or an increase in patient stress as indicated by an increase in patient activity and an increase in patient respiration level. An example of an implantable patient activity sensor includes an accelerometer.

In some examples, the implantable sensor 415 or sensors includes an implantable patient activity sensor and the system 400 includes a timer circuit 425 coupled to the trigger event detector 405. The first condition includes a detected sudden decrease in patient activity level. The sudden decrease can be indicated by a specified decrease in patient activity within a specified period of time as measured by the activity sensor.

In some examples, the ischemia detector 410 is enabled by duty-cycling the ischemia detector on and off. In an illustrative example, the ischemia detector is enabled every two hours. In some examples, the ischemia detector 410 is enabled by the trigger event detector using a circadian rhythm of a patient. In an illustrative example, the ischemia detector is enabled during a time of day where there is a higher risk of ischemia for the patient, such as early morning hours.

It can be seen that the trigger event detector 405 detects a first tier of events that may indicate ischemia which triggers the ischemia detector 410 that may include sensors and modules. In this way, battery power is preserved because the ischemia detector 410 is enabled when the first tier event or events indicate that myocardial ischemia has become more likely in the patient.

The ischemia detector 410 includes one or more implantable sensors 420. The implantable sensor 420 produces an electrical sensor signal related to one or more physiologic cardiovascular events in a subject that are indicative of ischemia. In some examples, the output of a combination of implantable sensors is used to detect a physiologic cardiovascular event. In some examples, an implantable sensor is used by both the trigger event detector 405 and the ischemia detector 410, as is indicated by the dashed line 430. In some examples, the ischemia detector 410 samples a signal produced by the implantable sensor 420 at a first rate, and enabling the ischemia detector 410 includes sampling the signal produced by the implantable sensor 420 at a different second rate. In an illustrative example, the second rate is a higher sampling rate.

According to some examples, the ischemia detector 410 includes one or more modules implementing functions and methods to recognize that a change in a sensor signal is indicative of ischemia. As described below, information related to the sensor signals may be communicated to an external device and the processor may operate on a computer system, such as a personal computer, server or other computer system.

In some examples, the ischemia detector 410 includes an implantable heart sound sensor. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole. A heart sound sensor produces an electrical signal which is representative of mechanical activity of a patient's heart. The heart sound sensor is disposed in a heart, or near the heart in a location where the acoustic energy can be sensed. In some examples, the heart sound sensor includes an accelerometer disposed in or near a heart. In another embodiment, the heart sound sensor includes a microphone disposed in or near a heart.

Monitoring heart sounds allows a physician to observe or assess the hemodynamic performance of a patient. A change in heart chamber contractility can accompany an ischemic event, and such a change can be measured using a heart sound sensor. Because ischemia is associated with a decrease in ventricular chamber contractility, ischemia is correlated to a decrease in the loudness of the S1 heart sound. An approach for monitoring heart sounds is found in Siejko et al., U.S. Patent Application Publ. No. 2004/0127792, entitled "Method and Apparatus for Monitoring of Diastolic Hemodynamics," filed Dec. 30, 2002, which is incorporated herein by reference.

In some examples, the ischemia detector 410 includes a heart sound monitoring module in communication with an implantable heart sound sensor to detect an ischemic event using a measured change in a heart sound signal from an established baseline heart sound signal. An approach for monitoring heart sounds to detect ischemic events is found in Zhang et al., U.S. patent application Ser. No. 11/148,107, entitled "Ischemia Detection Using a Heart Sound Sensor," filed Jun. 8, 2005, which is incorporated herein by reference.

An ischemic event may be reflected in a change in a time interval between a heart sound and another physiologic cardiovascular event. To detect a change in such a time interval, a baseline time interval may be established between first and second events, such as a first detected physiologic cardiovascular event and a second detected physiologic cardiovascular event for example. At least one of the first and second physiologic events includes a heart sound event detected from a heart sound signal. Examples of such time intervals include, without limitation, a time interval from a Q-wave of a QRS complex to an S1 or S2 heart sound, a time interval from a R-wave to an S1 or S2 heart sound, and a time interval between two heart sounds.

An ischemic event is determined to have occurred when a measured subsequent change from the established baseline time interval occurs with a time constant that is within a specified range of time constants. For example, assume a running average is used to measure a baseline time interval. An episode may be determined to be an ischemic event if the measured change from the baseline time interval occurs relatively suddenly with a time constant that ranges from a few seconds to a few minutes (e.g., five minutes) from the last value used for the running average. In some examples, the measured change in an interval must exceed a specified threshold change within the specified time duration. An approach for detecting ischemia from changes in time intervals of physiologic events that include heart sounds is described in Patangay et al., commonly assigned, copending, U.S. patent application Ser. No. 11/625,003, entitled "Ischemia Detection Using Heart Sound Timing," filed Jan. 19, 2007, which is incorporated herein by reference.

An ischemic event may include abnormalities in a subject's ECG. Thus, in some examples, the ischemia detector 410 includes an implantable cardiac signal sensing circuit adapted to sense intracardiac electrograms and one or more modules to detect the ECG abnormality. In some examples, the ischemia detector detects the abnormality from a decrease in amplitude of a patient's QRS cardiac signal complex accompanied by an increase in the duration of the QRS complex. In some examples, the ECG abnormality can be manifested in a subject's S-wave to T-wave ("ST") interval. The ischemia detector 410 establishes a baseline for a patient's ECG and detects ischemia by determining that an S-wave to T-wave ("ST") interval of the ECG that deviates by a specified amount from an ST interval of a baseline ECG. An approach for detecting myocardial ischemia from changes in electrocardiogram signals is described in Benser, U.S. Pat. No. 6,108,577, entitled "Method and Apparatus for Detecting Changes in Electrocardiogram Signals," filed Apr. 26, 1999, which is incorporated herein by reference.

In some examples, the ischemia detector 410 uses signals from a combination of sensors to detect ischemia. An approach for detecting ischemia using a combination of heart sound monitoring and ECG monitoring is found in the previously mentioned Zhang et al., U.S. patent application Ser. No. 11/148,107.

Table 1 below shows an example where the output of an implantable heart sound sensor and an implantable cardiac signal sensing circuit are blended according to a decision matrix. The ischemia detector 410 applies a low, medium, or high weight to the strength of a measured S4 heart sound change. Similarly, the ischemia detector 410 applies a low, medium, or high weight to a measured deviation in an ST interval in an ECG signal. In one example, the weights are applied based on amplitude changes from a corresponding patient-specific baseline.

If the weights of the measured signals are both low, the ischemia detector 410 has a low confidence level that an ischemic event occurred. If the weights of the measured signals are both high, the ischemia detector 410 has a high confidence level that an ischemic event occurred. The rest of the decision matrix can be programmed based on factors such as history of the patient or experience of the caregiver.

TABLE 1

ST deviation

| | | | |
|---|---|---|---|
| High | – | – | High Confidence Level |
| Medium | – | – | – |
| Low | Low Confidence Level | – | – |
| | Low | Medium | High |

S4 Heart Sound

In some examples, the ischemia detector 410 applies one or more fuzzy logic rules that use the weights to merge the sensor outputs and the measured change in the heart sound signal to determine whether an ischemic event occurred. The ischemia detector 410 may use any combinations of the sensors described herein to detect ischemia.

In some examples, implantable cardiac signal sensing circuit includes a wireless subcutaneous ECG sensing circuit. A wireless ECG is a signal approximating the surface ECG and is acquired without using surface (skin contact) electrodes. An example of a circuit for sensing the wireless ECG is discussed in McCabe et al., U.S. Patent Application Publ. No. 2005/0197674, entitled "Wireless ECG in Implantable Devices," filed on Mar. 5, 2004, which is incorporated herein by reference.

Myocardial ischemia may result in a change in a patient's cardiac activation sequence. In some examples, the ischemia detector 410 detects a change in the cardiac activation to detect ischemia. In some examples, the ischemia detector 410 receives a plurality of composite electrical sensor signals associated with a plurality of implantable cardiac signal sensing circuits. The ischemia detector performs a source separation, and produces one or more cardiac signal vectors associated with all or a portion of one or more cardiac activation sequences based on the source separation. An approach to detecting ischemia using a wireless ECG-based ischemia detector is discussed in Zhang et al., U.S. Patent Application Publ. No. 2006/0116593, entitled "Cardiac Activation Sequence Monitoring for Ischemia Detection," filed on Mar. 14, 2005, which is incorporated herein by reference.

Myocardial ischemia may result in a change in right ventricle and left ventricle synchrony. In some examples, the ischemia detector 410 includes implantable cardiac signal sensing circuits coupled to electrodes placed in or near the right ventricle and the left ventricle. This allows the ischemia detector 410 to detect ischemia from a change in RV/LV synchronization. In an example, the ischemia detector 410 includes a cardiac lead that includes one or more electrodes placed in a coronary vein lying epicardially on the left ventricle via the coronary vein. This provides sensing of contractions of the left ventricle.

In some examples, the ischemia detector 410 includes an implantable cardiac blood pressure sensor. When about 25% of the myocardium of the left ventricle becomes acutely ischemic, the end-diastolic pressure and volume increases. Typically, in an acute coronary occlusion event, the LVEDP can increase by 10 mmHg and the rate of pressure change in the LV ("LV dP/dt") can decrease by 500 mmHg/s in less than one minute. Examples of sensors that can detect an increase in left ventricle filling pressure include an implantable cardiac pressure sensor and a heart sound sensor. In some examples, the ischemia detector 410 includes an implantable cardiac pressure sensor to measure chamber pressure of the left ventricle. In an example, a pressure sensor is implanted in a coronary vessel to determine left ventricle pressure by direct measurement of coronary vessel pressure.

A description of systems and methods that use such an implantable pressure sensor is found in Salo et al., U.S. Pat. No. 6,666,826, entitled "Method and Apparatus for Measuring Left Ventricular Pressure," filed Jan. 4, 2002, which is incorporated herein by reference. Other cardiac pressure sensors examples include a right ventricle (RV) chamber pressure sensor, a pulmonary artery pressure sensor, and a left atrial chamber pressure sensor.

During diastole, the pulmonary arterial (PA) diastolic pressure generally correlates to LVEDP. Thus, the change in LVEDP during a reduction of blood supply to the myocardium of the LV may be detected by monitoring PA diastolic pressure. A reduction of blood supply, such as ischemia or myocardial infarction, to at least a portion of a heart, such as the myocardium of the LV, can generally be detected using information from an implantable PA pressure sensor.

To detect a reduction in blood supply to a portion of the heart, a pulmonary arterial pressure (PAP) signal is sensed, such as by using an implantable PA pressure sensor for example. At least one feature of the PAP signal is identified. Examples of the identifiable feature include, among other things, at least one detected amplitude, at least one detected magnitude, at least one detected peak, at least one detected valley, at least one detected value, at least one detected change, at least one detected increase, at least one detected decrease, and at least one detected rate of change in the at least one PA pressure characteristic. The time between two occurrences of the identifiable feature is then determined. The feature and the time interval between two occurrences of the feature can be identified by using a signal processor.

One or more time intervals may be used to compute an indication of a reduction of blood supply to at least a portion of a heart. As an example, if the identifiable feature is a magnitude of PA end-diastolic pressure ("PAEDP"), a 25% reduction of blood supply to at least a portion of the heart can be computed if the interval between a detected PAEDP magnitude having a first level and a detected PAEDP magnitude having a second level that exceeds the first level by a certain amount (e.g., 50 mmHg) occurs within a certain amount of time (e.g., 45 seconds). An approach for detecting a reduction in blood supply to a portion of the heart using PA pressure is described in Zhang et al., commonly assigned, copending, U.S. patent application Ser. No. 11/624,974, entitled "Ischemia Detection Using Pressure Sensor," filed Jan. 19, 2007, which is incorporated herein by reference.

Myocardial ischemia may results in regional shortening of a heart wall. This change can be manifested as left ventricle (LV) wall motion abnormality for example. In some examples, the ischemia detector 410 includes an implantable cardiac wall motion sensor to detect a reduction in LV contractility that often results from myocardial ischemia. Examples of such sensors measure cardiac wall motion using heart sounds, acceleration signals, and/or cardiac impedance.

Regional shortening causes changes in the heart sounds detectable with a heart sound sensor. A description of systems and methods for sensing wall motion is found in the commonly assigned, co-pending U.S. patent application Ser. No. 11/135,985, entitled "Systems and Methods for Multi-Axis Cardiac Vibration Measurements," filed May 24, 2005, which is incorporated herein by reference.

An accelerometer can be used to provide acceleration signals each indicative of regional cardiac wall motion. One or more accelerometers can be incorporated into a portion of a lead positioned on or in the heart. The accelerometers detect the wall motion abnormality as an abrupt decrease in the amplitude of local cardiac accelerations.

A cardiac impedance sensor senses an electrical impedance signal between electrodes interposed in the heart. For example, in FIG. 2 a cardiac impedance sensor can sense intracardiac impedance of the right ventricle 205A between an electrode placed at the apex of the right ventricle 205A and an electrode placed in the right atrium 200A. A predetermined excitation current is delivered between the electrodes and the impedance is determined from a voltage sensed between the electrodes. A transthoracic impedance of a subject can be measured between the ring electrode 225 and can electrode 250 or header electrode 260.

A cardiac impedance sensor can be used to track an impedance signal along with cardiac contractions and create a baseline impedance or normal impedance signal pattern. Because cardiac impedance is responsive to cardiac contractions, changes due to regional shortening may change the morphology of the impedance swings that occur with each cardiac contraction. In some examples, the ischemia detector 410 includes a module to compare impedance signal morphology to a baseline signal pattern. When the pattern is significantly different, e.g. based on fiducial points in the signal or based on an amplitude distance between the signals (such as a mean absolute deviation or a root-mean-square (RMS) difference), an ischemic event is declared. In some examples, the ischemia detector 410 compares the morphology by assigning a morphology score to the impedance signal. An ischemic event is declared if the morphology score is different from a predetermined threshold score by a specified amount. In some examples, the morphological changes may be confirmed by other sensor measurements.

In some examples, a cardiac impedance sensor is used to measure impedance at different frequencies of excitation current. A myocardium in an ischemic state exhibits substantially different impedance responses at different frequencies, such as between 1 KHz and 500 KHz, while lung tissue and edema fluid do not exhibit much change at frequencies below 1 MHz. The degree of myocardial ischemia has little effect on impedance measurements made at 500 KHz, whereas at 1 KHz the degree of ischemia has a significant effect on the impedance. As such, multi-frequency measurements can be taken, and the results can be used to classify impedance changes as resulting from pulmonary edema or myocardial ischemia, for example.

Systems and methods to measure cardiac impedance at different frequencies are described in Belalcazar et al., U.S. Pat. Publication No. 20060184060, entitled "Pathology Assessment with Impedance Measurements using Convergent Bioelectric Lead Fields," filed Feb. 15, 2005, which is incorporated herein by reference. Current is injected between a pair electrodes and a potential difference is measured between a second pair of electrodes near an assessment site within the body. The measurements are taken while the current is injected at 1 kHz and at 500 kHz. An impedance value is calculated at based on the potential difference and the current injection, and is used to assess a pathology near the assessment site.

In some examples, the ischemia detector 410 includes an implantable cardiac temperature sensor. In some examples, the implantable cardiac temperature sensor is included in a lead system implanted into the coronary sinus of a patient. The implantable cardiac temperature sensor measures the temperature of the blood returning through the coronary sinus after having passed through myocardial tissue. As a byproduct of normal cardiac function, the heart generates heat. This heat is extracted by the perfusing blood. The blood exits through the coronary veins into the coronary sinus before passing into the right atrium and right ventricle. The blood is then pumped through the lungs where the excess heat is removed and passed out of the body with the exhaled air.

The useful work ($W_u$) performed by the left ventricle relates to the volume of blood moved through the ventricle, whereas the heat output from the left ventricle is related to total work ($W_T$). The difference in temperature between blood entering the left ventricle and blood in a coronary vein is related to left ventricular work. An increase in $W_T$, or cardiac temperature as a surrogate measurement, that is not accompanied by other indications of increased activity or patient exertion may indicate a lowering of efficiency of a patient's hemodynamic system due to myocardial ischemia.

An approach to sensing temperature within a coronary vein is found in Salo, Patent Application Publ. No. 2003/0125774, entitled "Method and Apparatus for Monitoring Left Ventricular Work or Power," filed Dec. 31, 2001, which is incorporated herein by reference.

In some examples, the ischemia detector 410 includes an implantable oxygen saturation sensor. An oxygen saturation sensor produces an electrical sensor signal related to changes in the fluid oxygen saturation associated with the heart's mechanical activity, contractility, and blood flow. An ischemic event can be accompanied by a change in heart chamber contractility. This change in contractility may be manifested as reduced levels in blood oxygen saturation levels. An approach for using an implantable sensor to measure blood oxygen saturation levels is found in Thompson, U.S. Pat. No. 5,342,406, entitled "Oxygen Sensor Based Capture Detection for a Pacer," filed Oct. 7, 1992, which is incorporated herein by reference.

In some examples, the ischemia detector 410 includes an implantable chemical sensor. Myocardial ischemia may be accompanied by an increase in the blood lacetic acid level in the coronary sinus. The increase in blood lacetic acid level is accompanied by a decrease in blood pH that is detectable with a chemical sensor. An approach to providing a chemical sensor in a coronary sinus is found in Kane et al., U.S. patent application Ser. No. 11/383,933, entitled, "Implantable Medical Device with Chemical Sensor and Related Methods", filed May 17, 2006, which is incorporated herein by reference.

Figure 5:
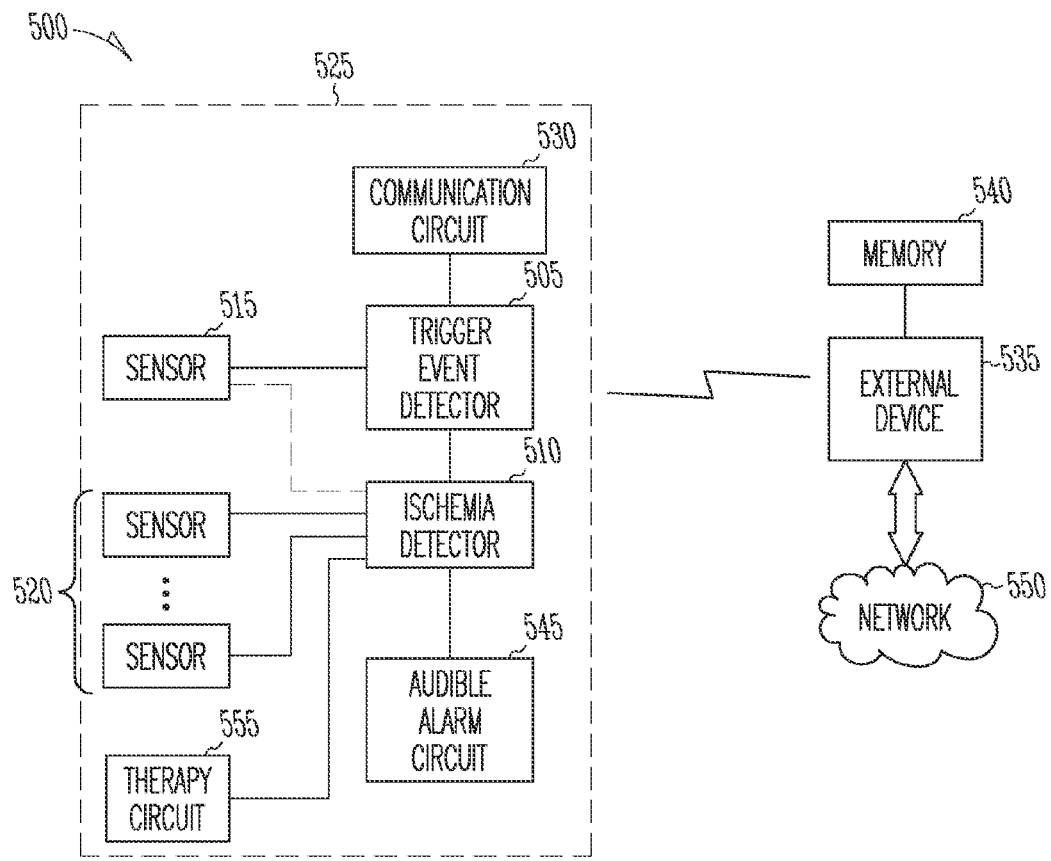
FIG. 5 is a block diagram of portions of an example of another system to detect myocardial ischemia.

FIG. 5 shows a block diagram of portions of another example of a system 500 to detect myocardial ischemia. The system 500 includes a trigger event detector 505 and an ischemia detector 510 in an implantable medical device 525 (IMD). The IMD 525 further includes a communication circuit 530 to provide communication with an external device 535. The first condition that causes the trigger event detector 505 to enable the ischemia detector 510 includes the external device 535 communicating with the MD 525 to enable the ischemia detector 510. Such a communication may include communicating a command to enable the ischemia detector 510 for example. The system 500 may include one or more sensors 515 in electrical communication with the trigger event detector 505. The first condition may include one or more physiologic events detected by the trigger event detector 505.

The ischemia detector includes one or more implantable sensors 520. Some implantable sensors provide signals that are susceptible to physiological noise. For example, the amplitude of the heart sounds and the frequency components of the heart sounds of the person are different when a person is standing or sitting than when the person is lying down. Knowing when a change in the signal provided by an implantable sensor is due to physiological noise rather than due to ischemia reduces the chances of the ischemia detector 510 indicating a false positive. In addition to changes in patient posture, other sources of physiologic noise include changes in patient activity and changes in a patient's heart rate.

To reduce false positives, the sensor signals provided by the implantable sensor 520 or sensors of the ischemia detector 510 can be measured at various postures, levels of activity, and heart rates, i.e., in the presence of physiologic noise. The measurements are stored in memory and are trended separately for the various conditions. In some examples, the IMD 525 communicates information related to the sensor signals to the external device 535 where the measurements are stored in a memory 540. In some examples, the memory 540 is included in the IMD 525. The measurements can be trended using memory 540 in either the external device 535 or the IMD 525. This removes the physiologic noise from the measurements. The ischemia detector 410 includes a trending module that may be part of the IMD 525 or the external device 535.

In some examples, the ischemia detector 510 includes at least one first implantable sensor 520 that produces a first electrical sensor signal related to one or more physiologic cardiovascular events in a subject that are indicative of ischemia, and an implantable posture sensor. The implantable posture sensor produces an electrical signal related to posture of the subject. The ischemia detector 510 trends the first electrical sensor signal in relation to posture of the subject.

In some examples, the ischemia detector 510 includes at least one first implantable sensor 520, and an implantable activity sensor. The implantable activity sensor produces an electrical signal related to activity of the subject and the ischemia detector 510 trends the first electrical sensor signal in relation to activity of the subject. In some examples, the ischemia detector 510 includes at least one first implantable sensor 520, and an implantable cardiac signal sensing circuit to produce an electrical signal related to heart rate of a patient. The ischemia detector 510 trends the first electrical sensor signal in relation to heart rate of the subject.

In some examples, IMD 525 includes an audible alarm circuit 545 coupled to the ischemia detector 510. The ischemia detector 510 provides an audible alarm, such as a buzzer or other audible indication, if an episode of myocardial ischemia is declared upon detecting the second condition. The detection of ischemia may trigger a drug delivery device to automatically administer a drug. In some examples, the IMD 525 communicates an indication of myocardial ischemia to the external device 535 and the external device 535 provides audible alarm, a visual alarm such as by a display, or both an audible and a visual alarm. The visual alarm provided by the external device may include text with instructions for the patient, such as to take some predetermined medication, adjust medication or to seek immediate medical assistance.

In some examples, the external device 535 includes a remote server in communication with the IMD 525 over a communications or computer network 550. In some examples, the IMD 525 may communicate with the external device 535 over the network 550 using a second intermediate external device, such as a repeater. In some examples, the system 500 is included in a guardian system for early detection of myocardial ischemia.

In some examples, the memory 540 stores a log containing information related to ischemia for a patient. The log contains information related to an ischemic episode such as the time and the duration of the episode. Sampled electrical signals used to detect the episode may be communicated to the memory and stored in the log. Examples of these signals include signals from any of the sensors discussed herein. The log may also include information related to the activity or exertion of the patient as deduced from the sensor signals. In some examples, an entry is made in the log only upon confirmation of an ischemic episode. In some examples, an entry is made in the log for at least some detected false alarms, such as when one or more predetermined sensor signals exceed a predetermined threshold value.

In some examples, the IMD 525 includes a therapy circuit 555 coupled to the ischemia detector 510. The ischemia detector 510 initiates a device therapy if an episode of myocardial ischemia is declared upon detecting the second condition. In some examples, the therapy circuit 555 is coupled to one or more cardiac leads and delivers an electrical therapy to a patient. In some examples, the electrical therapy includes cardioversion/defibrillation therapy. In some examples, the electrical therapy includes neuro-stimulation therapy. In some examples, the therapy circuit 555 initiates a drug therapy.

In some examples, the electrical therapy includes pacing therapy. In some examples, the ischemia detector 510 initiates one or more cardiac protection pacing sequences in response to the detection of the ischemic event. The one or more cardiac protection pacing sequences may include alternating pacing and non-pacing periods. The non-pacing periods each have a non-pacing duration during which none of the pacing pulses is delivered. An approach to protection pacing in response to detecting ischemia is found in Baynham et al., U.S. patent application Ser. No. 11/129,050, entitled "Method and Apparatus for Cardiac Protection Pacing," filed May 13, 2005, which is incorporated herein by reference.

In some examples, the therapy circuit 555 is operable to provide a chronic therapy and to initiate a post-ischemic therapy is response to a detected ischemic event. The chronic pacing therapy adjusts one or more global pacing parameters to reduce the overall workload on a patient's heart, and the post-ischemia pacing therapy adjusts one or more regional pacing parameters to provide pre-excitation of the ischemic region to reduce the stress and work load of the ischemic region. An approach to providing chronic and post-ischemic therapy is found in Brockway et al., U.S. patent application Ser. No. 11/207,251, entitled "Method and Apparatus for Delivering Chronic and Post-Ischemia Cardiac Therapies," filed Aug. 19, 2005, which is incorporated herein by reference.

The functions and methods described herein are typically implemented in software or a combination of software and human implemented procedures in one embodiment. The software typically comprises computer executable instructions stored on computer readable media such as memory or other type of storage devices. Computer readable media can also reside at a remote site and the software is downloadable to a machine from the remote site.

Figure 6:
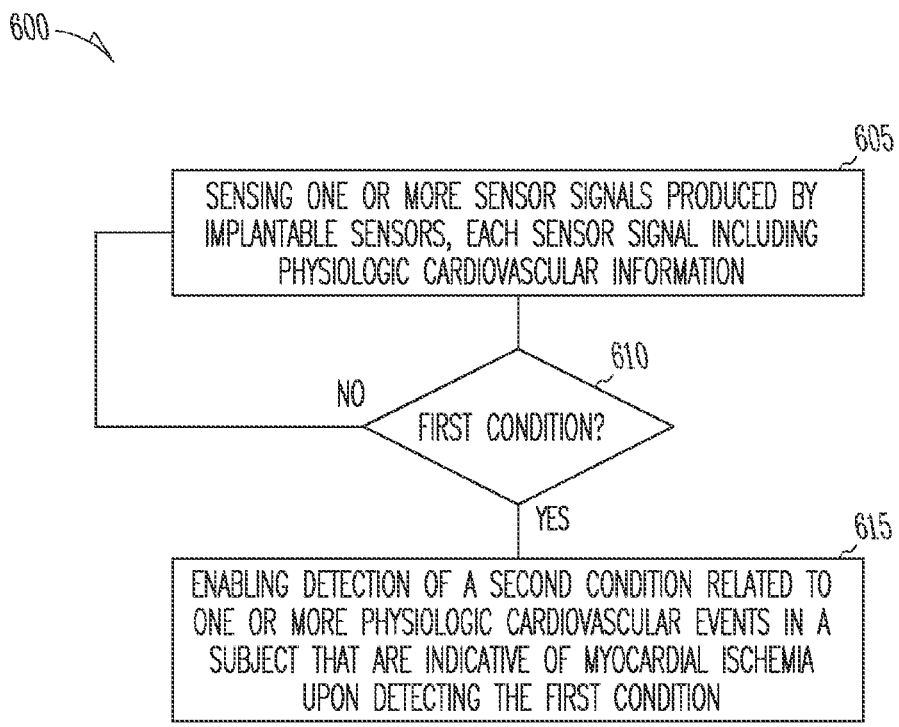
FIG. 6 is a flow diagram of an example of a method to detect myocardial ischemia.

FIG. 6 is a diagram of a method 600 for detecting myocardial ischemia. At 605, one or more sensor signals produced by one or more implantable sensors are sensed. Each sensor signal includes physiologic cardiovascular information. At 610, it is determined whether a first condition occurred. In some examples, the first condition includes one or more physiologic events that may indicate that the patient has experienced myocardial ischemia. The physiologic event associated with the first condition may be a highly sensitive indication of ischemia (i.e., the resulting detection is likely to be over-inclusive of events that are indicative of ischemia), but need not be specific to ischemia. In some examples, a baseline is established for the one or more sensor signals. A condition is detected when a deviation from the established baseline occurs in the signal that exceeds a predetermined threshold difference value.

In some examples, determining the first condition includes determining that an increase in heart rate exceeds a predetermined heart rate threshold exceeds a predetermined heart rate threshold value. In some examples, determining the first condition includes determining that a rate of change in a heart rate of a subject exceeds a predetermined heart rate threshold value.

In some examples, determining the first condition includes detecting decrease in heart rate variability (HRV). In some examples, determining the first condition includes a detecting decrease in respiratory sinus arrhythmia (RSA). In some examples, determining the first condition includes detecting an abnormal cardiac rhythm. An abnormal cardiac rhythm can be detected using an assessment of heart rhythm stability when a subject experiences a sudden increase in heart rate, or by comparing the morphology of a sensed cardiac signal to the morphology template stored in a memory.

In some examples, determining the first condition includes detecting an increase in patient exertion or an increase in patient stress. In some examples, determining the first condition includes detecting a sudden decrease in patient activity level, such as by determining a decrease in patient activity within a predetermined period of time. In some examples, determining the first condition includes monitoring the circadian rhythms of a patient, such as according to a time of day where there is a higher risk of ischemia for the patient. In some examples, determining the first condition includes detecting any combination of the events.

If it is determined that the first condition occurred at 610, detection of a second condition related to one or more physiologic cardiovascular events in a subject is enabled at 615. The second condition includes one or more events that are indicative of myocardial ischemia upon detecting the first condition. The second condition or conditions preferably include physiologic cardiovascular events more specific to myocardial ischemia than the first condition. In some examples, the first condition that enables the detection of the second condition is provided by an external device. For example, the external device communicates a command to an IMD to enable detecting the second condition.

Enabling detection of the second condition can include powering-on at least a portion detection circuitry. Enabling can also include causing a branch to execute instructions in a module that detects the second condition. In some examples, detecting the second condition includes sampling electrical signals provided by implantable sensors. The signals are sampled at a first sampling rate to establish a baseline for the sensor signals. Enabling detection of the second condition includes enabling sampling of the sensor signals at a second sampling rate. In some examples, the second rate is an increased rate compared to the first sampling rate. This allows battery power to be preserved when not actively trying to detect the second condition.

In some examples, the second condition includes a deviation in the ST segment of a sensed ECG signal from an established baseline for the segment. In some examples, the second condition includes a change in the cardiac activation sequence. In some examples, the second condition includes a change in blood pressure from an established baseline blood pressure value. In some examples, the second condition includes a change in right ventricle and left ventricle synchrony. In some examples, the second condition includes a change in morphology of a sensed cardiac depolarization signal. In some examples, the second condition includes a decrease in measured cardiac blood oxygen saturation. In some examples, the second condition includes a change in cardiac wall motion.

In some examples, the method 600 includes sampling the sensor signals and trending the sensor signals in the presence of physiologic noise. Physiologic noise can be changes in the sampled sensor signals due to changes in patient posture, patient activity, or changes in a patient's heart rate. To remove the noise, the measurements from the sampled signals are trended separately at various postures, levels of activity, and heart rates. Changes in the sensor signals are then compared to the stored measurements. The trending can be done using memory in an IMD or the measurement can be communicated to an external device for trending.

In some examples, the method 600 includes communicating an alarm if an episode of myocardial ischemia is declared upon detecting the second condition. The alarm can be an audible alarm, such as a buzzer or other audible indication from an IMD. In some examples, an indication of myocardial ischemia is communicated from an IMD to an external device, and the external device provides an audible alarm, a visual alarm such as by a display, or both an audible and a visual alarm. The visual alarm provided by the external device may include text with instructions for the patient, such as to take some predetermined medication, adjust medication or to seek immediate medical assistance. In some examples, the external device communicated the alarm over a communications or computer network.

In some examples, the method 600 includes updating an ischemia log for a patient if an episode of myocardial ischemia is declared upon detecting the second condition. The log can be stored in a memory and contain information related to an ischemic episode such as the time and the duration of the episode. In some examples, sampled signals used to detect the episode may be communicated to the memory and stored in the log. The log may also include information related to the activity or exertion of the patient as deduced from the sensor signals. In some examples, the method 600 includes making an entry in the log only upon confirmation of an ischemic episode. In some examples, the method 600 includes making an entry in the log when one or more predetermined sensor signals exceed a predetermined threshold value.

In some examples, the method 600 includes initiating a device therapy if an episode of myocardial ischemia is declared upon detecting the second condition. The device therapy can include a drug therapy. In some examples, the device therapy includes electrical therapy such as cardioversion/defibrillation therapy, neuro-stimulation therapy, or pacing therapy.

Pacing therapy can include one or more cardiac protection pacing sequences in response to the detection of the ischemic event. The one or more cardiac protection pacing sequences may include alternating pacing and non-pacing periods. Pacing therapy may include a chronic pacing therapy and a post-ischemic pacing therapy. The chronic pacing therapy reduces the overall workload on a patient's heart, and the post-ischemia pacing therapy provides pre-excitation of the ischemic region to reduce the stress and work load of the ischemic region.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72 (b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising:
   an implantable trigger event detector, adapted to detect at least one first condition and to output a responsive trigger signal including information about whether the first condition has been detected, wherein the at least one first condition is indicative of at least a reduction in a patient's vagal response;
   an implantable cardiac signal sensing circuit in communication with the trigger event detector; and
   an implantable ischemia detector, adapted to detect a second condition indicative of one or more physiologic cardiovascular events in a subject that are indicative of ischemia, wherein the ischemia detector is coupled to the trigger event detector to receive the trigger signal, and wherein the ischemia detector is enabled upon the trigger signal indicating a decrease in heart rate variability (HRV).

2. The system of claim 1, further wherein the ischemia detector is enabled upon the trigger signal indicating that a heart rate exceeds a predetermined heart rate threshold value.

3. The system of claim 1, further wherein the ischemia detector is enabled upon the trigger signal indicating that a rate of change in heart rate exceeds a predetermined heart rate threshold value.

4. The system of claim 1, further including an implantable patient activity sensor and an implantable respiration sensor in communication with the trigger event detector, wherein the ischemia detector is enabled upon the trigger signal indicating at least one of an increase in patient exertion and an increase in patient stress.

5. The system of claim 1, further wherein the ischemia detector is enabled upon the trigger signal indicating an abnormal cardiac rhythm.

6. The system of claim 1, wherein the trigger event detector and the ischemia detector are included in an implantable medical device (IMD), wherein the system further includes an external device adapted to communicate with the IMD, and wherein the ischemia detector is enabled by the trigger event detector in response to a communication with the external device.

7. The system of claim 1, wherein the ischemia detector includes one or more implantable sensors from the group consisting of:
   a) a heart sound sensor;
   b) a cardiac blood pressure sensor;
   c) a cardiac signal sensing circuit adapted to sense intracardiac electrograms;
   d) a subcutaneous ECG sensing circuit;
   e) a cardiac wall motion sensor;
   f) a transthoracic impedance sensor;
   g) an intracardiac impedance sensor;
   h) a chemical sensor;
   i) an oxygen sensor;
   j) an accelerometer; and
   k) a temperature sensor.

8. The system of claim 1, wherein the ischemia detector includes:
at least one first implantable sensor, configured to produce a first electrical sensor signal related to one or more physiologic cardiovascular events in a subject that are indicative of ischemia; and
an implantable posture sensor configured to produce an electrical signal related to posture of the subject, and wherein the ischemia detector is configured to trend the first electrical sensor signal in relation to posture of the subject.

9. The system of claim 1, wherein the ischemia detector includes:
at least one first implantable sensor, configured to produce a first electrical sensor signal related to one or more physiologic cardiovascular events in a subject that are indicative of ischemia; and
an implantable activity sensor configured to produce an electrical signal related to activity of the subject, and wherein the ischemia detector is configured to trend the first electrical sensor signal in relation to activity of the subject.

10. The system of claim 1, wherein the ischemia detector includes:
at least one first implantable sensor, configured to produce a first electrical sensor signal related to one or more physiologic cardiovascular events in a subject that are indicative of ischemia; and
an implantable cardiac signal sensing circuit configured to produce an electrical signal related to heart rate of the subject, and wherein the ischemia detector is configured to trend the first electrical sensor signal in relation to heart rate of the subject.

11. The system of claim 1, wherein the trigger event detector and the ischemia detector are included in an implantable medical device (IMD), wherein the IMD further includes an audible alarm circuit coupled to the ischemia detector, and wherein the ischemia detector is configured to provide an audible alarm if an episode of myocardial ischemia is declared upon detecting the second condition.

12. The system of claim 1, wherein the trigger event detector and the ischemia detector are included in an implantable medical device (IMD), wherein the system further includes an external device adapted to communicate with the IMD, and wherein the IMD is configured to communicate an indication of myocardial ischemia to the external device.

13. The system of claim 12, wherein the external device includes a remote server in communication with the IMD over a communications or computer network.

14. The system of claim 1, further including a memory, in communication with the ischemia detector, to store a log containing information related to ischemia for a patient.

15. The system of claim 1, wherein the trigger event detector and the ischemia detector are included in an implantable medical device (IMD), wherein the IMD further includes a therapy circuit coupled to the ischemia detector, and wherein the ischemia detector is configured to initiate a device therapy if an episode of myocardial ischemia is declared upon detecting the second condition.

16. A system comprising:
an implantable trigger event detector, adapted to detect at least one first condition and to output a responsive trigger signal including information about whether the first condition has been detected, wherein the at least one first condition is indicative of at least a reduction in a patient's vagal response;
an implantable cardiac signal sensing circuit and an implantable respiration sensor in communication with the trigger event detector; and an implantable ischemia detector, adapted to detect a second condition indicative of one or more physiologic cardiovascular events in a subject that are indicative of ischemia, wherein the ischemia detector is coupled to the trigger event detector to receive the trigger signal, and wherein the ischemia detector is enabled upon the trigger signal indicating a decrease in respiratory sinus arrhythmia (RSA).

17. A system comprising:
an implantable trigger event detector, adapted to detect at least one first condition and to output a responsive trigger signal including information about whether the first condition has been detected, wherein the at least one first condition is indicative of at least a reduction in a patient's vagal response;
an implantable patient activity sensor and a timer circuit coupled to the trigger event detector; and
an implantable ischemia detector, adapted to detect a second condition indicative of one or more physiologic cardiovascular events in a subject that are indicative of ischemia, wherein the ischemia detector is coupled to the trigger event detector to receive the trigger signal, and wherein the ischemia detector is enabled upon the trigger signal indicating a decrease in patient activity level within a predetermined period of time.

18. A system comprising:
an implantable trigger event detector, adapted to detect at least one first condition and to output a responsive trigger signal including information about whether the first condition has been detected, wherein the at least one first condition is indicative of at least a reduction in a patient's vagal response;
a timer circuit coupled to the trigger event detector; and
an implantable ischemia detector, adapted to detect a second condition indicative of one or more physiologic cardiovascular events in a subject that are indicative of ischemia, wherein the ischemia detector is coupled to the trigger event detector to receive the trigger signal, and wherein the ischemia detector is enabled by the trigger event detector using a circadian rhythm when detecting the first condition.

19. A method comprising:
sensing one or more sensor signals produced by one or more implantable sensors, each sensor signal including physiologic cardiovascular information;
determining at least one first condition that is indicative of at least a reduction in a patient's vagal response; and
enabling detection of a second condition related to one or more physiologic cardiovascular events in a subject that are indicative of myocardial ischemia upon detecting the first condition, wherein determining the first condition includes detecting at least one physiologic event from the group consisting of:
a) a decrease in heart rate variability (HRV);
b) a decrease in respiratory sinus arrhythmia (RSA);
c) a predetermined decrease in patient activity level within a predetermined period of time; and
d) a time that is predetermined according to a patient circadian rhythm.

20. The method of claim 19, including:
sampling the sensor signals at a first sampling rate to establish a baseline for the sensor signals; and
wherein enabling detection of the second condition includes enabling sampling of the sensor signals at a different second sampling rate.

21. The method of claim 19, wherein determining the first condition further includes detecting at least one physiologic event from the group consisting of:
    a) an increase in heart rate that exceeds a predetermined heart rate threshold;
    b) an increase in a rate of change in heart rate exceeds a predetermined heart rate threshold value; and
    c) an abnormal cardiac rhythm.

22. The method of claim 19, wherein determining the first condition includes determining that an enable for detecting the second condition is communicated from an external device.

23. The method of claim 19, wherein detecting the second condition includes detecting one or more of:
    a) an ST segment deviation;
    b) a change in a cardiac activation sequence;
    c) a change in one or more heart sound features;
    d) a change in blood pressure from an established baseline blood pressure;
    e) a change in right ventricle and left ventricle synchrony;
    f) a change in morphology of a sensed cardiac depolarization signal;
    g) a decrease in cardiac blood oxygen saturation;
    h) a change in cardiac wall motion;
    i) a change in transthoracic impedance;
    j) a change in intracardiac impedance; and
    k) a change in cardiac temperature without an accompanying detected increase in patient exertion level.

24. The method of claim 19, further including:
    sampling the sensor signals;
    trending the sensor signals in the presence of physiologic noise; and
    using the trending to remove physiologic noise from the sampled signals.

25. The method of claim 19, further including communicating an alarm if an episode of myocardial ischemia is declared upon detecting the second condition.

26. The method of claim 19, further including updating an ischemia log for a patient if an episode of myocardial ischemia is declared upon detecting the second condition.

27. The method of claim 19, further including initiating a device therapy if an episode of myocardial ischemia is declared upon detecting the second condition.

28. A method comprising:
    sensing one or more sensor signals produced by one or more implantable sensors, each sensor signal including physiologic cardiovascular information;
    determining at least one first condition that is indicative of at least a reduction in a patient's vagal response, wherein determining the first condition includes determining a circadian rhythm of the subject; and
    enabling detection of a second condition related to one or more physiologic cardiovascular events in a subject that are indicative of myocardial ischemia upon detecting the first condition.

* * * * *

UNITED STATES PATENT AND TRADEMARK OFFICE
CERTIFICATE OF CORRECTION

PATENT NO. : 8,014,863 B2  
APPLICATION NO. : 11/625045  
DATED : September 6, 2011  
INVENTOR(S) : Yi Zhang et al.

It is certified that error appears in the above-identified patent and that said Letters Patent is hereby corrected as shown below:

On the Title Page, Item (75), in "Inventors", line 2, delete "Pittsburg, PA" and insert -- Pittsburgh, PA --, therefor.

In column 1, line 2, below "HEART ATTACK OR ISCHEMIA DETECTOR" insert -- CROSS-REFERENCE TO RELATED APPLICATIONS --.

In column 20, line 30, in Claim 2, delete "further wherein" and insert -- wherein --, therefor.

In column 20, line 33, in Claim 3, delete "further wherein" and insert -- wherein --, therefor.

In column 20, line 43, in Claim 5, delete "further wherein" and insert -- wherein --, therefor.

Signed and Sealed this  
Twenty-fifth Day of October, 2011

David J. Kappos  
*Director of the United States Patent and Trademark Office*